United States Patent [19]
Grandia et al.

[11] Patent Number: 5,827,204
[45] Date of Patent: Oct. 27, 1998

[54] MEDICAL NONINVASIVE OPERATIONS USING FOCUSED MODULATED HIGH POWER ULTRASOUND

[76] Inventors: Willem Grandia, 919 Sunset Dr., Costa Mesa, Calif. 92627; Yoseph Bar-Cohen, 3721 Fuchsia St., Seal Beach, Calif. 90740

[21] Appl. No.: 863,162

[22] Filed: May 27, 1997

Related U.S. Application Data

[63] Continuation of Ser. No. 756,351, Nov. 26, 1996, abandoned.
[51] Int. Cl.$^6$ ........................................... A61N 7/00
[52] U.S. Cl. .............................. 601/2; 600/427; 600/439; 601/4
[58] Field of Search ............................. 601/2–4; 600/439, 600/427

[56] References Cited

U.S. PATENT DOCUMENTS

| | | | |
|---|---|---|---|
| 4,905,672 | 3/1990 | Schwarze et al. | 601/4 |
| 5,209,221 | 5/1993 | Riedlinger | 601/2 |

*Primary Examiner*—Ruth S. Smith
*Attorney, Agent, or Firm*—Walter A. Hackler

[57] ABSTRACT

Medical noninvasive operations using focused modulated high power ultrasound in accordance with the present invention generally includes a transmitter for exciting a multifrequency ultrasound wave for causing vaporous cavitation bubbles in a small focal zone of a medical target region. Focused ultrasound can be used for both dissolving tissues as well as causing clots in order to destroy cancerous growths. The multifrequency wave includes an underlying low frequency signal for enabling optimal growth of microbubbles and at least one high frequency signal for enabling a narrow zone of focus of the ultrasound. A cavitation monitor may be provided for sensing a level of cavitation as well as providing feedback to the transmitter. In addition, an imaging system is provided for enabling viewing of the medical target area during the therapy.

20 Claims, 5 Drawing Sheets

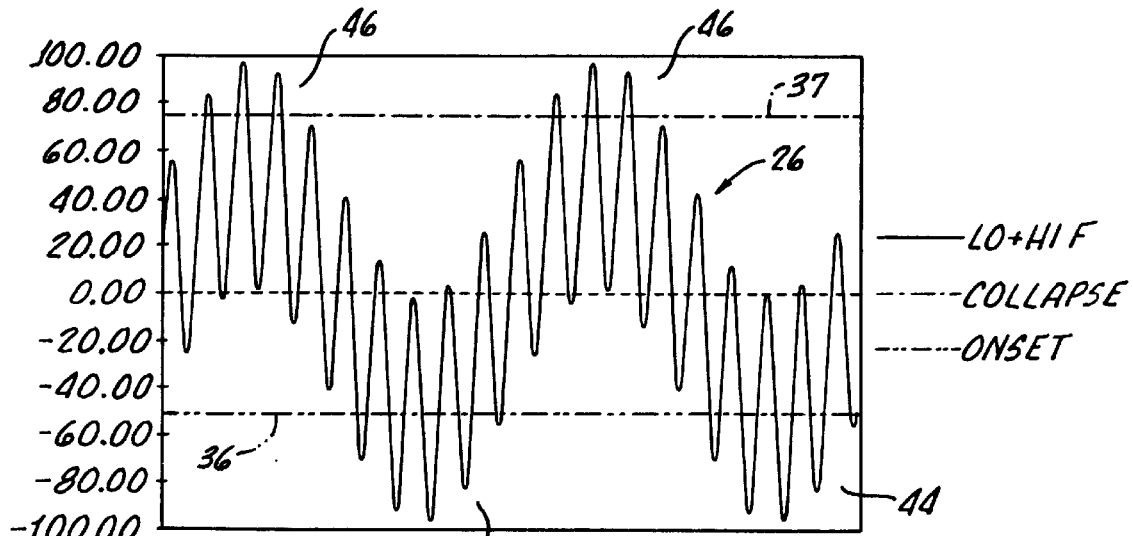
_FIG. 2a._
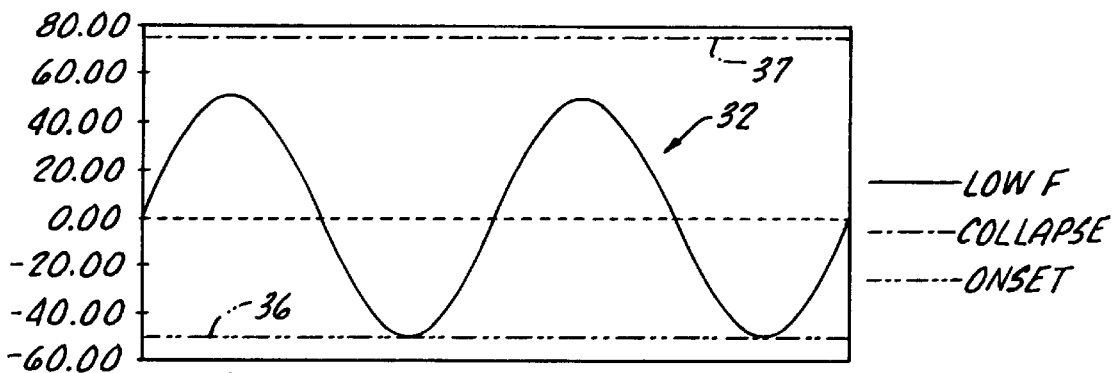
_FIG. 2b._
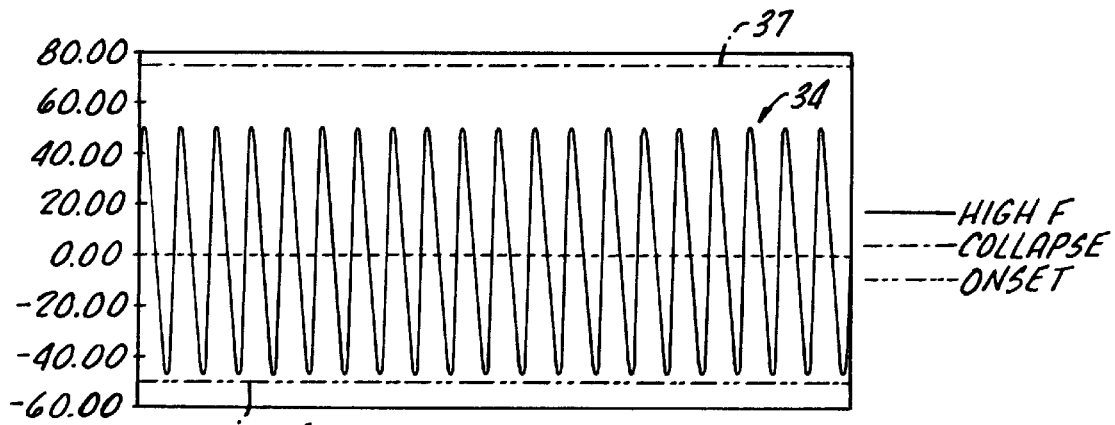
_FIG. 2c._

MEDICAL NONINVASIVE OPERATIONS USING FOCUSED MODULATED HIGH POWER ULTRASOUND

This application is a continuation application of U.S. Ser. No. 08/756,351 filed Nov. 26, 1996, now abandoned.

The present invention generally relates to noninvasive medical procedures using ultrasonic energy and more specifically relates to medical apparatus and method for noninvasive surgical procedures using focused modulated high powered ultrasound for dissolving thrombi, promoting blood clotting and destroying malignant and benign tumors in living tissue.

Medical procedures are needed for controlled regions of the human body using noninvasively delivered high powered ultrasonic energy. It is known that ultrasonic waves offer a means for delivering high powered mechanical energy for disintegration of medical targets by heating the target with focused ultrasound or by ablation of the target with ultrasonic shock waves.

For example, U.S. Pat. No. 5,402,792 to Fry et al. discloses a system for reducing the mass of gall stones by radiating the gall bladder with ultrasonic energy transmitted transcutaneously and having a frequency range of 200 KHz to 250 KHz.

Other medical applications of ultrasonic energy include radiating ultrasonic energy into a thrombus, i.e. blood clot, in a living vessel, by means of a catheter having a probe on an end thereof which has a spherical, oscillating tip. The probe is sized for intravascular insertion such that the tip may be positioned adjacent the blockage.

Ultrasound has also been used in conjunction with medicinal fluids, for example thrombolytic agents, to enhance the efficiency of the medicinal fluid, for example, in dissolving a thrombus or other blockage of a venous or arterial vessel. For example, U.S. Pat. No. 5,509,896 to Carter et al., which is incorporated herein by specific reference thereto, teaches the use of external ultrasonic energy to enhance thrombolytic action of a thrombolytic agent during its activity in dissolving an vessel obstruction.

It is known that ultrasonic energy for use in medical treatment by heating or dissolution of the target, with or without the aid of medicinal fluids, is most effective in the low frequency range of about 25 KHz to about 100 KHz, which produces high power mechanical vibrations capable of heating tissue and dissolving clot formations. However, in this low frequency range, the ultrasonic energy can not be focused using conventional techniques due to its large wavelengths, i.e for a range of 25 kHz, the ultrasound wavelength is about 6 centimeters long and thus cannot be focused to a diameter smaller than about the size of a wavelength, or about 6 centimeters. This minimal focal area is often much larger than the size of the medical target, thus enhancing risk of injury to tissue adjacent the target.

On the other hand, methods for focusing of high frequency ultrasound, for example in the megahertz range, are well known, and commercially available transmitters can produce focal zones having diameters of fractions of millimeters. However, ultrasound in this frequency range does not contain the high power needed to effectively destroy the medical target by heat or mechanical vibration and without the assistance of medicinal agents.

In a U.S. Patent to Rolt et al., an apparatus is disclosed which utilizes two ultrasound beams of about equal frequencies but from distinct, and physically separate sources, which cross each other confocally at a target area, for example a cancerous tumor. According to Rolt et al., the apparatus provides a focused area of high energy ultrasound energy which heats and destroys the cancerous tumor but does not injure adjacent tissue. Unfortunately, this apparatus requires two or more ultrasound radiating elements, and relies upon a complex aiming device which electronically directs the ultrasound beams in order to cross the beams at the medical target.

Cavitation is a physical phenomenon which occurs as a result of pressure changes in a fluid, including the radiation of high powered ultrasound through blood. More specifically, cavitation is the formation and collapse of microbubbles in a fluid due to pressure in the fluid reaching certain critical levels. In a fluid, when ultrasound waves are introduced at high power, the rarefaction, i.e. low pressure, part of the wave will reach a point that induces cavitation bubble formation as a result of the fluid reaching the vapor pressure level. During the compression part of the wave, the microbubbles violently collapse, i.e. implode, producing thermal energy and shock waves.

Up to this point, little medical use has been made of the complex relationship between ultrasound energy and the cavitation of fluids, when in fact high powered mechanical energy is available by these means, but only if it can be effectively controlled. Accordingly, this is a primary object of the present invention.

There is a need for a medical apparatus and method which enables noninvasive surgical operations using high powered, low frequency ultrasound that can be narrowly focused, and cavitation resulting therefrom precisely controlled, in order to not only dissolve vascular obstructions but to promote clotting in order to stop bleeding, as well as destroy cancerous growths.

SUMMARY OF THE INVENTION

Noninvasive surgical apparatus in accordance with the present invention, for affecting a medical target in a living being by destruction of undesired tissue or by coagulation of blood, generally comprises a focusing transmitter which provides means for transmitting high power, multifrequency ultrasound signals into a medical target region, wherein said multifrequency ultrasound signal has carefully chosen parameters for controlling and optimizing the effects of cavitation in a region comprising the medical target and surrounding fluid. The multifrequency signal generally comprises a low frequency ultrasound signal having one or more high frequency ultrasound signals superimposed thereon.

As will be discussed in greater detail hereinafter, the low frequency signal provides means for controlling growth of cavitation microbubbles in the medical target region. The low frequency signal is induced at a level slightly below that required for causing cavitation, i.e. below the cavitation threshold, of the target region. The high frequency signal or signals is modulated or superimposed on the low frequency signal to exceed the cavitation threshold.

More specifically, the low frequency component of the modulated multifrequency signal may have a frequency of less than about 100 kHz, but preferably at about 25 kHz for enabling optimal bubble growth. The high frequency signal is between about 200 kHz and about 2.5 MHZ for enabling a narrow zone of focus.

The result is a high powered ultrasound signal that will cause large vaporous cavitation bubbles in a small, confined area, i.e. the focal zone. Means are provided for variably positioning the focal zone of the multifrequency signal into the medical target region in order to cause vaporous cavitation at specific locations therein.

Pulsed or continuous ultrasound may be used, depending upon the treatment desired. Mechanical vibrations resulting from imploding cavitations are useful for disintegrating blood clots and other medical targets. Pulsed high power ultrasound, which causes minimal heating of the target area, is preferable for purposes of tissue disintegration. Alternatively, by transmitting the ultrasound at a different energy level, for example by using continuous rather than pulsed high power ultrasound, the present invention can be used for coagulating blood and causing clots.

The creation of clots is desirable for destroying cancerous growths or other vascular abnormalities. More particularly, when high power ultrasound is carefully controlled in a confined area, the heating effect of cavitation can be used for creating clots in order to prevent a blood supply from nourishing and supporting the growth. In a similar respect, the present invention can be used for coagulating blood in order to stop uncontrolled bleeding in instances where invasive surgical procedures are not feasible.

The apparatus and method of the present invention can be used for a variety of noninvasive medical procedures, to heat and destroy tissues, dissolve blood clots, cataract, arthero sclerosis and cancerous tissue, as well as control internal bleeding without damage to skin, peripheral tissues or organs.

Medical apparatus in accordance with the present invention preferably includes a three part system comprising a high powered focusing transmitter, a cavitation sensor and imaging means for allowing visualization of the medical target area during treatment.

BRIEF DESCRIPTION OF THE DRAWINGS

The present invention will be more clearly understood with reference to the following detailed description when considered in conjunction with the following drawings of which:

FIG. 2a is a diagram of the multifrequency ultrasound wave, comprising a low frequency component modulated with a high frequency component, the wave being represented as pressure that is varying as a function of time along a wave path;

FIG. 2b is a diagram of the low frequency component of the modulated signal shown in FIG. 2a, said low frequency component set below a cavitation threshold of the target region and providing means for controlling growth of cavitation bubbles in the target region;

FIG. 2c is a diagram of the high frequency component of the modulated signal shown in FIG. 2a, which enables narrow focusing of the modulated signal and spacial control of an area of cavitation.

DETAILED DESCRIPTION

Figure 1:
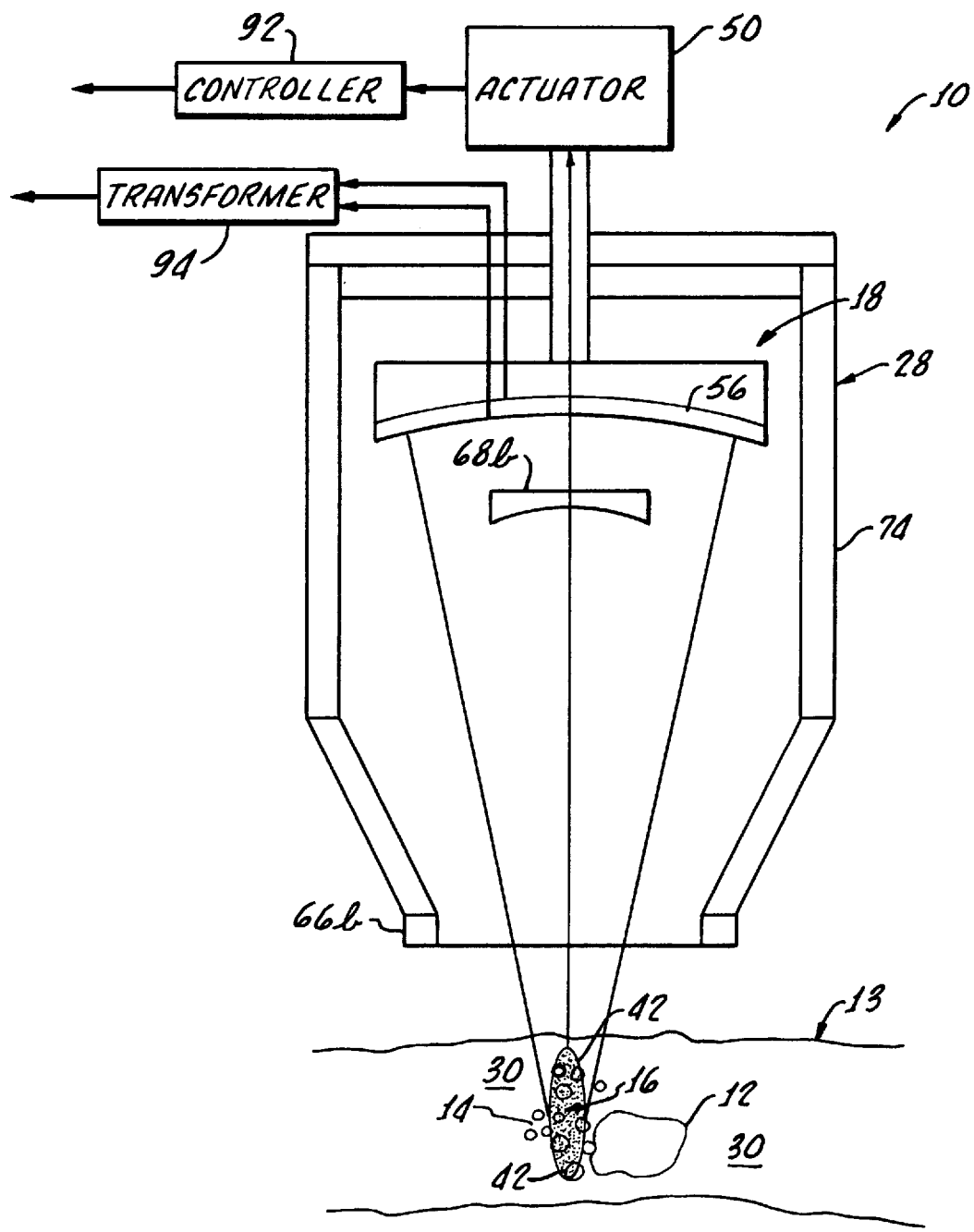
FIG. 1 shows an embodiment of noninvasive surgical apparatus in accordance with the present invention, including a transmitter, used for transmitting a high power modulated ultrasound wave into a medical target region, cavitation sensor means for monitoring and optimizing formation of cavitation in the target region and providing feedback to the transmitter, and an imaging means for allowing visualization of the medical target during treatment.

Turning now to FIG. 1, noninvasive surgical apparatus 10 in accordance with the present invention is shown as being used to dissolve a medical target 12, such as a blood clot in a vessel 13, using high energy vaporous cavitation 14 confined to a small focal zone 16.

The apparatus 10 generally includes at least one ultrasonic transmitter 18 which provide means for inducing a modulated multifrequency ultrasound wave 26, such as that represented in FIG. 2a. The transmitter 18 is preferably disposed within a probe 28 which is adapted for transmitting the ultrasound transcutaneously into a region 30 containing the medical target 12.

A multifrequency ultrasonic wave 26 represented in FIG. 2a is comprised of individual components shown in FIGS. 2b and 2c and is made by modulating a low frequency signal 32 with at least one high frequency signal 34. A cavitation formation threshold, represented by line 36, and a cavitation collapse threshold, represented by line 37, are shown in each of the FIGS. 2a–2c. The significance of the cavitation threshold will be discussed in detail hereinafter.

The underlying low frequency signal 32 is preferably less than about 100 kHz and more preferably is about 25 kHz. As shown in FIG. 2b, the low frequency signal 32 is induced at a level slightly below said cavitation formation threshold 36. In other words, the low frequency signal 32 is induced at a level less than that required for cavitation to form.

The high frequency signal 34 may be in the megahertz range, but may range from about 200 kHz up to about 2.5 MHz. Modulation of the low and high frequency signals results in the multifrequency signal 26 which exceed the cavitation threshold 36.

Importantly, the modulated wave 26 has frequency and amplitude parameters chosen for both maximizing the cavitation effect of the wave 26 when transmitted into the medical target region 30 and establishing the narrow focal zone 16 where such cavitation will occur.

Focusing megahertz frequency ultrasound is a well established technology as the size of a the focal zone of an ultrasonic wave is dependent upon its wavelength. However, high frequency ultrasonic waves alone can not deliver the power needed for surgical operations. On the other hand, low frequency ultrasonic waves can be transmitted at high powers sufficient to perform such surgical tasks by heating or dissolving unwanted tissue, but are difficult to focus using conventional techniques.

The apparatus 10 and method of the present invention provides for focusing high powered ultrasonic energy in a small area for use in noninvasive surgical procedures.

Ultrasonic energy is useful for dissolving tissues and heating tissues due to formation and violent collapse of cavitation bubbles 42 (see FIG. 1). Cavitation 14 occurs in a fluid as a result of pressure changes therein, such as by the radiation of ultrasound through blood. The ultrasound must be radiated at an amplitude level sufficient to exceed a critical "threshold" level of the fluid in order to cause cavitation.

The amount of energy that is released during implosive collapse of cavitations depends on the size of the bubbles, ambient pressure, amount of dissolved gases, viscosity, surface tension, frequency and duration of ultrasonic energy.

In principle, there are two types of cavitation bubbles, i.e. (1) low intensity microbubbles that are created by gaseous cavitation, and (2) high intensity microbubbles produced by vaporous cavitation. The present invention utilizes the effect of high intensity vaporous cavitation. Vaporous cavitation implosions produce a violent effect which can be useful for medical purposes only if the region in which cavitation takes place is spatially controlled, as to not damage adjacent healthy tissues.

The effectiveness of cavitation in medical operations is dominated by the critical radius of the cavitation bubbles at which bubble size is unstable and implodes. Referring to FIG. 2a, at high powers, as the pressure of the liquid, e.g. blood, drops during the rarefaction part 44 of an ultrasonic wave cycle, the liquid reaches a critical vapor pressure allowing the formation of cavitation bubbles. When the pressure increases during the compression part 46 of the wave cycle, the bubbles reach a critical pressure at which they collapse, resulting in a violent effect.

During the collapse of cavitation bubbles, peak temperature values of up to 13,000 degrees Fahrenheit and pressures as high as 75,000 psi can be observed. These extreme temperatures and pressure values are realized at the center of the cavitation bubble at the final stage of its collapse.

Importantly, the size of the cavitation bubbles decreases with increases in ultrasound frequency. Cavitation bubbles grow larger at lower frequencies due to the longer period between the rarefaction and the compression part of the wave. In other words, a longer wavelength allows the bubbles to grow larger before they collapse. The apparatus and method in accordance with the present invention enables large cavitation bubble growth dependent on the wavelength of the low frequency ultrasound signal.

Thus, the low frequency ultrasound signal 32 shown in FIG. 2b is used to control the growth of cavitation bubbles 42 in the medical target region 30. It is the high frequency signal 34 which enables confinement, or narrow focusing of the area undergoing high intensity vaporous cavitation. The focal zone 16 of the modulated wave 26 is dependent upon the high frequency signal 34.

Preferably, the apparatus 10 of the present invention may include means, for example a piezoelectric actuator 50 for positioning the focal zone 16 at the desired location in the patient. More particularly, the actuator 50 functions to control death of the focal zone 16 by pushing the transmitter 18 to the desired position within the probe 28.

The transmitter 18 may comprise a combination of transducers, or a single focused transducer 56 which is driven to produce simultaneously two or more frequencies in, such as the high frequency signal 34 and low frequency signals 32, in either continuous or tone burst mode. The choice of continuous or tone burst mode will depend upon the desired treatment being administered. The low frequency signal 32 and high frequency signal 34 can be excited by the single focused transducer 56 as radial and harmonic components respectively.

For example, the transducer 56 may include a diameter of about 10 centimeters which has a frequency mode related thereto of about 25 kHz, in order to produce the low frequency signal 32.

The ultrasonic waves 26 are produced in either a continuous or tone burst mode, depending upon the particular treatment being conducted.

For example, the multifrequency signal 26 may be transmitted in bursts to enhance operation efficiency and to control the effect of temperature rise and cavitation implosion. High temperatures are useful for cancer cell destruction they may have a negative effect on efforts to destroy blood clots. Therefore, a delay between consecutive pulses can be used when destroying blood clots, allowing cooling time between pulses. Short bursts and long delay causes the formation of cavitation with minimum heating, thus enhancing the blood clot disintegration mechanism.

On the other hand, the creation of blood clots may be used for destroying cancerous growths or other vascular abnormalities. More particularly, when high power ultrasound is carefully controlled in a confined area, the heating effect of cavitation can be used for creating clots in order to prevent a blood supply from nourishing and supporting the abnormal growth. In this way, focused ultrasound can be used to shrink or debulk primary as well as metastatic tumors.

When such clot creation is desirable, the focused transmitter 18 may be operated in a continuous mode, rather than pulsed, or may be operated in a pulsed mode using long pulses and short delay.

It should be appreciated that in a similar respect, the present invention can be used for coagulating blood in order to stop uncontrolled bleeding in instances where invasive surgical procedures are not feasible. Importantly, as will be discussed hereinafter, the present invention enables precise control of the effectiveness of the high power ultrasound, whether being used for disintegration of tissue or for clot creation.

Within the focal zone 16 of the multifrequency wave, said focal zone having a size dependent on the highest frequency component, vaporous cavitations are formed during the rarefaction portion of the multifrequency wave, where the liquid pressure reaches fluid vapor pressure. The focal zone of the focused modulated high power transmitter 18 is defined by a focal zone of the high frequency signal, where both the low frequency and high frequency signals are superimposed and reach a pressure drop below the level required for cavitation, i.e the cavitation formation threshold 36.

The dimensions of the focal zone 16 may be controlled by selecting a curvature of the focused modulated high power transmitter 18 and the high frequency value.

In addition as hereinabove noted, depth of the focal zone 16 may be controlled by the piezoelectric actuator 50 which provides means for variably positioning the focal zone. More particularly, the actuator 50 pushes the transmitter and imaging probes to the desired position in the probe 28.

The treated area, such as a cancer for example, may cause a high attenuation of the ultrasonic wave. In this case, treatment may need to be performed initially from the deepest portion of the medical target and moved progressively upward during the treatment.

By using the heating effect of focused ultrasound, cancerous growths may be destroyed by heating the growth directly, without causing damage to peripheral healthy tissue. In addition, as discussed hereinabove, a blood supply supporting an abnormal growth may be disrupted.

A method in accordance with the present invention may include the step of positioning the focal zone into a medical target region surrounding, or adjacent to, an abnormal growth. The growth may be for example, a cancerous tumor or other vascular abnormality. The modulated wave is transmitted at an energy level sufficient to cause thrombosis, i.e. clotting of blood, of a blood supply supporting the growth. By using the heating effect of focused high power ultrasound, blood flow to the growth may be interrupted by as an effective form of medical treatment.

Figure 3:
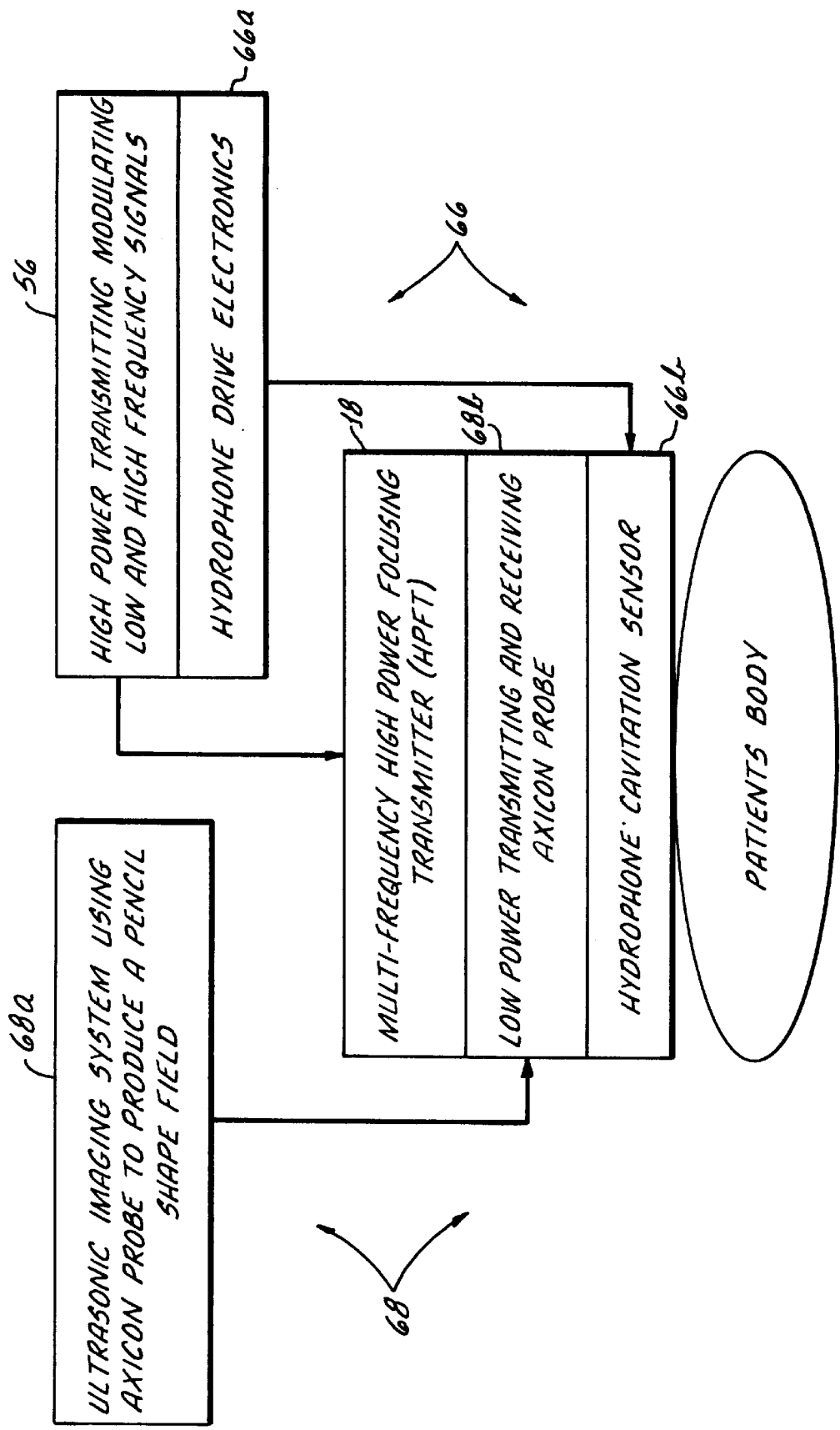
FIG. 3 shows a block diagram of the embodiment of the present invention shown in FIG. 1.

Referring now to FIGS. 1 and 3, in addition to the focusing transmitter 18, the present invention preferably includes a cavitation monitor 66 including hydrophone drive electronics 66a and hydrophone cavitation sensor 66b as well as imaging means 68 including system electronics 68a and axiom transducer or probe 68b for enabling viewing of the medical target region 30 during treatment.

In this embodiment, the focusing transmitter 18, cavitation monitor 66 and imaging means 68 may be combined within the probe 28, with each element cooperating to enable optimization of the effectiveness of the high powered ultrasound.

FIG. 3 shows a block diagram of the components of the present invention including the combined transmitter/cavitation-sensor/imaging probe 28 that is shown in FIG. 1. The multifrequency high power transmitter 18 as described hereinabove and the cavitation sensor 66b disposed within a probe housing 74, as shown in FIG. 1. The cavitation sensor 66b may comprise a high frequency hydrophone, for example Model SPRH-S- 1000 and amplifier A101 that operates up to the megahertz range (Hydrophone Specialty Engineering Associates, Milipitas, California) and a low frequency hydrophone for example, Model 8103 for up to 180 kHz (Bruel & Kjaer, Denmark), as means for enabling direct monitoring of cavitation formation and providing feedback to the transmitter 18 in order to enable optimization of cavitation. Monitoring of cavitation is performed during positioning of the focal zone in the target region, in other words, during the surgical operation. The hydrophone enables optimization of cavitation by monitoring the ultrasonic emission that is associated with the formation of cavitation.

In addition, a low power ultrasonic field is transmitted through the medical target area in order to produce a visual image of the area being treated. This may be accomplished, for example, by use of an array transducer ultrasonic imaging system, such as Model UT-3D (QMI, Costa Mesa, Calif.) or by use of a high frequency ultrasonic transducer 66b, forming a part of an imaging axicon transmitter and receiver, which produces a pencil shaped, low power high frequency ultrasound field in the medical target region 30. The image formed thereby is preferably a cross section view of the target region, and is formed by combining the ultrasonic data from the probe with the linear location of the high power focusing transmitter. X-Y coordinates are defined as the linear location and the depth information and the image consists of the time dependent data measured by the probe.

Figure 4:
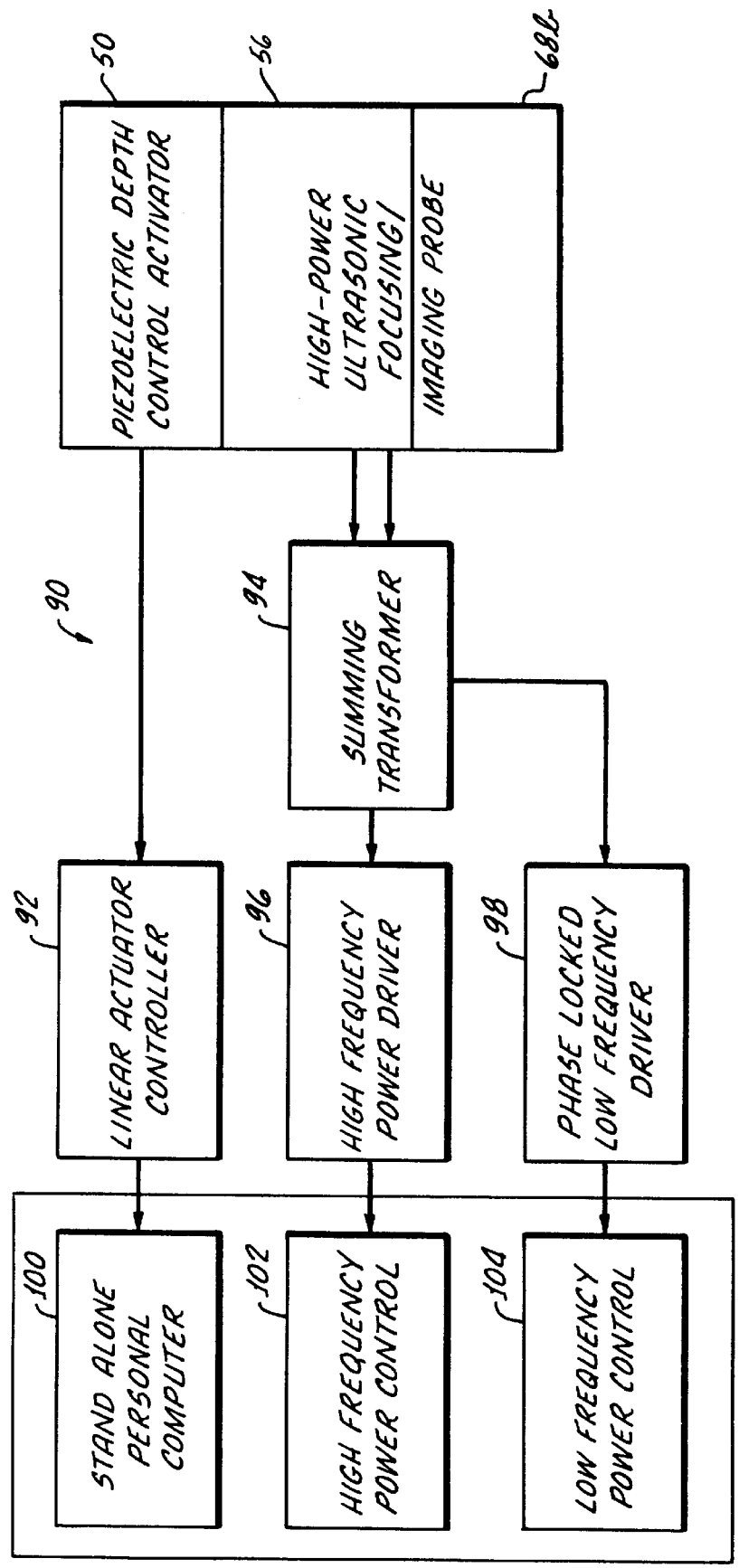
FIG. 4 shows block diagram of suitable drive electronics for the transmitter and cavitation formation feedback.
Figure 5:
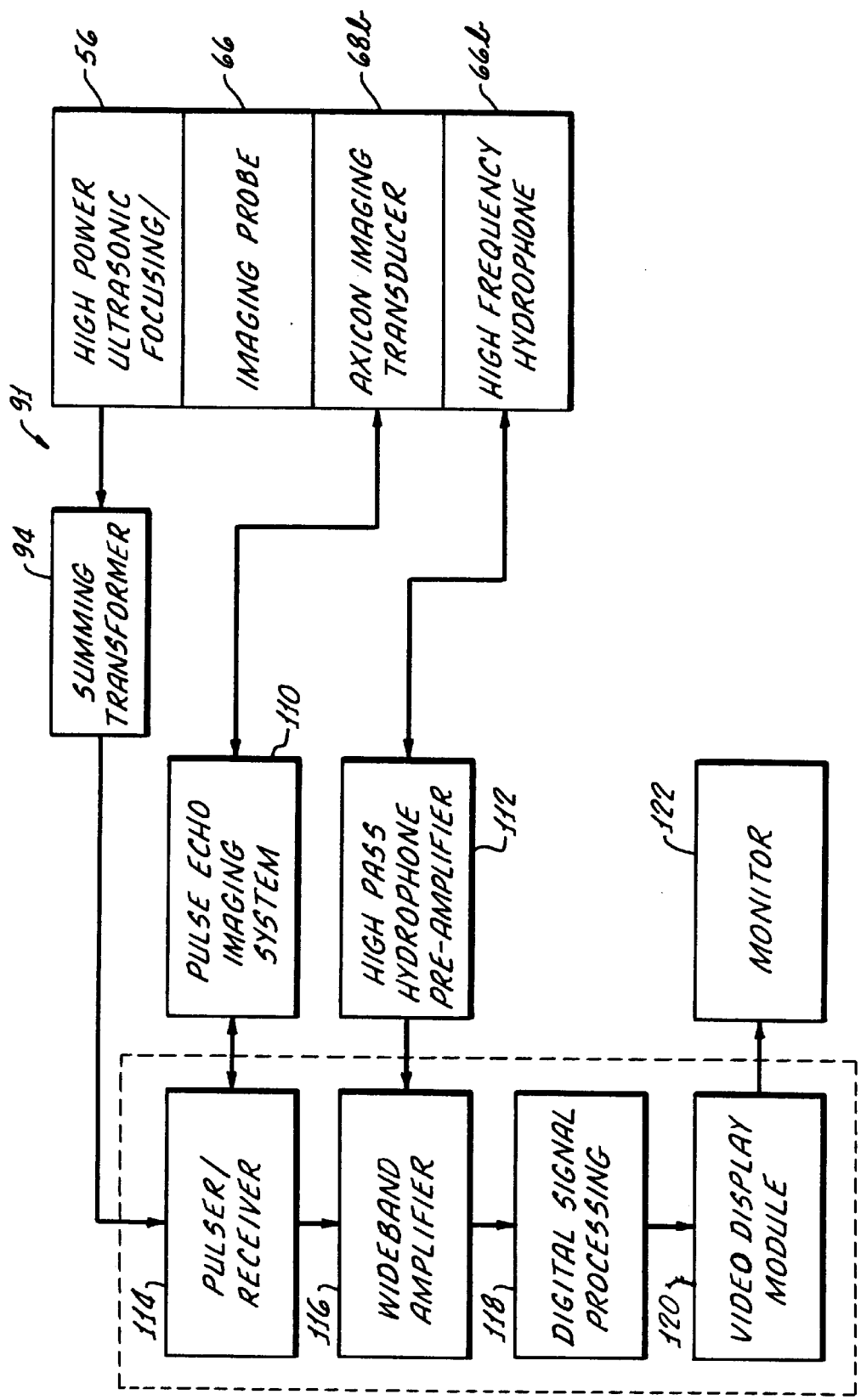
FIG. 5 shows a block diagram of suitable electronics for the imaging means.

FIGS. 4 and 5 show suitable drive electronics in accordance with the present invention. In particular, FIG. 4 shows high power drive electronics 90 for the combined transmitter/imaging and monitoring probe and FIG. 5 shows an electronic block diagram 90 for ultrasonic imaging.

As shown in FIG. 4, a high power drive electronics 90 for the piezoelectric depth control actuator 50, the high power ultrasonic transducer 56 and the imaging probe 68b includes a linear actuator controller 92 and a summing transformer 94 interconnected with a high frequency power driver 96 and a phase locked low frequency driver 98. Interconnected therewith, is a personal computer 100 high frequency power control 102 and a low frequency power control 104.

Turning to FIG. 5, which is a schematic view of the ultrasonic imaging electronics 91. The electronics 91 includes a pulse echo imaging system 110, a high pass hydrophone preamplifier 112, a pulse receiver 114, a wide band amplifier 116, a digital signal processor 118, a video display module 120 and monitor 122, all of these components being conventional in construction.

Although there has been hereinabove described medical noninvasive surgical operations using focused modulated high power ultrasound and method therefor, in accordance with the present invention, for the purpose of illustrating the manner in which the invention may be used to advantage, it will be appreciated that the invention is not limited thereto. Accordingly, all modifications, variations, or equivalent arrangements which may occur to those skilled in the art should be considered to be within the scope of the invention as defined in the appended claims.

What is claimed is:

1. Noninvasive surgical apparatus for affecting a medical target in a living being by destruction of undesired tissue or coagulation of blood, said apparatus comprising:

low frequency ultrasound means, including a low frequency ultrasound signal, for controlling growth of cavitation microbubbles in a medical target region, said low frequency ultrasound signal having an amplitude below a cavitation threshold of the target region, means for superimposing at least one high frequency ultrasound signal onto the low frequency signal in order to produce a modulated ultrasound signal having an amplitude that exceeds said cavitation threshold, said modulated signal having a focal zone of a size determined by the high frequency signal; and means for positioning the focal zone of the modulated signal into the medical target region in order to cause vaporous cavitation therein.

2. The noninvasive surgical apparatus according to claim 1 wherein the low frequency signal has a frequency of less than about 100 kHz.

3. The noninvasive surgical apparatus according to claim 2 wherein the high frequency signal has a frequency of between about 200 kHz and about 2.5 MHZ.

4. The noninvasive surgical apparatus according to claim 1 wherein the low frequency signal has a frequency of about 25 kHz.

5. The noninvasive surgical apparatus according to claim 4 wherein the high frequency signal has a frequency of between about 200 kHz and about 2.5 MHz.

6. The noninvasive surgical apparatus according to claim 1 further comprising hydrophone means for monitoring a formation of the vaporous cavitation in the target region.

7. The noninvasive surgical apparatus according to claim 6 further comprising imaging means for producing a visual image of the medical target region in order to enable observation of the region during destruction of unwanted tissue or coagulation of blood therein.

8. The noninvasive surgical apparatus according to claim 1 wherein the means for positioning includes a piezoelectric actuator.

9. Noninvasive surgical apparatus comprising an ultrasound transmitter, including:

a source of a high frequency ultrasound signal, a source of a low frequency ultrasound signal, said low frequency ultrasound signal having an amplitude below a cavitation threshold of a medical target region in order to enhance bubble growth during vaporous cavitation and means for superimposing the high frequency signal and the low frequency signal in order to produce a modulated, multifrequency signal; and means for focusing the multifrequency signal into the medical target region in order to produce vaporous cavitation therein.

10. The noninvasive surgical apparatus according to claim 9 wherein the low frequency signal has a frequency of less than about 100 kHz.

11. The noninvasive surgical apparatus according to claim 10 wherein the high frequency signal has a frequency of between about 200 kHz and about 2.5 MHz.

12. The noninvasive surgical apparatus according to claim 9 wherein the low frequency signal has a frequency of about 25 kHz.

13. The noninvasive surgical apparatus according to claim 12 wherein the high frequency signal has a frequency of between about 200 kHz and about 2.5 MHz.

14. The noninvasive surgical apparatus according to claim 9 wherein further comprising hydrophone means for monitoring a formation of the vaporous cavitation in the medical target region.

15. The noninvasive surgical apparatus according to claim 14 further comprising imaging means for producing a visual image of the medical target area in order to enable observation of the medical target area during destruction of unwanted tissue or coagulation of blood therein.

16. A method for performing noninvasive surgery using modulated high powered ultrasound, said method comprising the steps of:

inducing a low frequency ultrasound signal at an amplitude below a cavitation threshold of a medical target region in order to control growth of cavitation microbubbles in the target region;

superimposing a high frequency signal onto the low frequency signal in order to produce a modulated signal having an amplitude that exceeds said cavitation threshold, said modulated signal having a focal zone of a size determined by the high frequency signal; and positioning the focal zone of the modulated signal into the medical target region in order to cause vaporous cavitation therein.

17. The method according to claim 16 wherein the step of inducing a low frequency signal comprises inducing a low frequency signal of less than about 100 kHz.

18. The method according to claim 17 wherein the step of inducing a low frequency signal comprises inducing a low frequency signal of less than about 25 kHz.

19. The method according to claim 16 wherein the step of inducing a high frequency signal comprises the step of inducing a ultrasound signal of between about 200 kHz and about 2.5 MHZ.

20. The method according to claim 17 further comprising the steps of monitoring the vaporous cavitation during the step of positioning the focal zone into the medical target and, producing a visual image of the medical target region in order to enable observation of the region.

* * * * *